(12) United States Patent
Egan et al.

(10) Patent No.: US 7,146,278 B2
(45) Date of Patent: Dec. 5, 2006

(54) METHOD OF SELECTING MARKER MOLECULES FOR PREDICTION OF MOLECULAR ACTIVITY

(75) Inventors: William J. Egan, Burlington, NJ (US); Steven L. Dixon, Yardley, PA (US)

(73) Assignee: Accelrys Software Inc., San Diego, CA (US)

( * ) Notice: Subject to any disclaimer, the term of this patent is extended or adjusted under 35 U.S.C. 154(b) by 0 days.

(21) Appl. No.: 09/919,739

(22) Filed: Jul. 31, 2001

(65) Prior Publication Data

US 2003/0073128 A1 Apr. 17, 2003

(51) Int. Cl.
*G06F 19/00* (2006.01)
*G06G 7/58* (2006.01)

(52) U.S. Cl. .............. 702/19; 703/2; 703/11; 702/27

(58) Field of Classification Search ............ 702/19, 702/27
See application file for complete search history.

(56) References Cited

U.S. PATENT DOCUMENTS

| 6,434,542 B1 | 8/2002 | Farman et al. |
| 2003/0611186 | 3/2003 | Farman et al. |

FOREIGN PATENT DOCUMENTS

| WO | WO 98/47087 | 10/1998 |
| WO | WO 00/62251 | 10/2000 |

OTHER PUBLICATIONS

Stanton, et al.; *J. Chem. Inf. Comput. Sci.*, vol. 39, No. 1, 1999; "Application of Nearest-Neighbor and Cluster Analyses in Pharmaceutical Lead Discovery," pp. 21-27.
Ghuloum, et al., *J. Med. Chem.*, vol. 42, No. 10, 1999, "Molecular Hashkeys: A Novel Method for Molecular Characterization and Its Application for Predicting Important Pharmaceutical Properties of Molecules," pp. 1739-1748.
Brown, et al., *J. Chem. Inf. Comput. Sci.*, vol. 36, No. 3, 1996, "Use of Structure-Activity Data To Compare Structure-Based Clustering Methods and Descriptiors for Use in Compound Selection," pp. 572-584.
Dixon, et al., "One-dimensional molecular representations and similarity calculations: methodology and validation", J. Med. Chem., vol. 44, pp. 3795-3809, (2001).
Saiakhov, et al., "Multiple computer-automated structure evaluation model of the plasma protein binding affinity of divers drugs", Perspectives in Drug Discovery and Designs, vol. 19, pp. 133-155, (2000).

*Primary Examiner*—Marjorie A. Moran
*Assistant Examiner*—Carolyn L. Smith
(74) *Attorney, Agent, or Firm*—Knobbe Martens Olson & Bear LLP

(57) ABSTRACT

A method predicts at least one property of a candidate molecule. A set of reference molecules is classified as either possessing or not possessing at least one property. A subset of the molecules is selected from which a plurality of marker molecules is chosen. The marker molecules are used to predict whether the candidate molecule possesses at least one property.

5 Claims, 5 Drawing Sheets

METHOD OF SELECTING MARKER MOLECULES FOR PREDICTION OF MOLECULAR ACTIVITY

BACKGROUND OF THE INVENTION

1. Field of the Invention

The invention relates to methods and systems for constructing models to predict molecular activity, and further relates to a model for predicting protein binding.

2. Description of the Related Art

Drugs may bind to a variety of components in the blood, including albumin, $a_1$-acid glyciprotein (AAG), lipoproteins, immunoglobulins, sex hormone binding globulins, and erythrocytes. Drugs which are $\geq 90\%$ protein bound in human serum are generally considered "highly bound". Some foreknowledge of the protein binding characteristics of a molecule would help provide a better estimate of the pharmacodynamics and pharmacokinetics of the molecule. Clearance depends significantly upon volume of distribution, which in turn depends upon the fraction of the drug in plasma which is unbound, $f_u$. Highly protein bound drugs, having low $f_u$, have lower free concentrations because the drug-protein complex cannot diffuse to reach the receptor, and this lowers the pharacodynamic response. One example is that the $f_u$ of phenytoin is more useful than the total plasma concentration of phenytoin for discriminating toxic responses to that drug. In addition, hepatic extraction is directly proportional to $f_u$. Glomerular filtration by the kidney does not occur for highly protein bound drugs, as the drug-protein complexes are too large to be filtered. The maximum oral bioavailability is directly related to the hepatic extraction ratio, which is in part dependent upon the $f_u$. Disease states causing significant drop in serum albumin, e.g. nephrotic syndrome, where serum albumin concentrations are halved, cause a corresponding 2-fold decrease in half-life for clofibrate. Competitive displacement of a drug from its protein binding site by other highly protein bound drugs has been theorized to lead to adverse events due to the increase in plasma concentration of the displaced drug or altered pharmacokinetics.

A variety of techniques have been developed for predicting protein binding. Lipophilicity has been repeatedly found to be significant factor in protein binding. This is not surprising, because some lipophilic character is usually required for interaction at receptor sites in proteins. Thus, high logP (octanol-water partition coefficient) has been found to be associated with high protein binding. Another predictive model is based on performing structural comparisons between a molecule with unknown behavior and a set of "marker molecules" having known behavior. A method of this type is known as the LLC hashkey method. The hashkey method randomly selects a relatively small set of molecules (20–200) to produce a molecular representation of the entire chemical space of interest. Similarities derived from 3-D molecular surface properties are computed from all molecules of interest to the chosen hashkey molecules, and properties are predicted using hashkey vectors and some form of computational model, e.g., a neural network or KNN.

Historically, efforts to build predictive models for protein binding have been only partially successful. Austel and Kutter reviewed 39 structure/activity prediction models for protein binding and concluded that the models "have shown that within a series of closely related compounds protein binding increases with lipophilicity. Differences between individual structural types are not well explained and cannot be predicted." (Austel, V.; Kutter, E. Absorption, Distribution, and Metabolism of Drugs. In *Quantitative Structure-Activity Relationships of Drugs*; Topliss, J. G., Ed.; Academic Press: New York, 1983, pp 437–496.) What is needed a more accurate model for predicting molecule behavior such as protein binding.

SUMMARY OF THE INVENTION

In one embodiment, a method of activity model development is provided in which a set of reference molecules is classified as either possessing or not possessing at least one property. A subset of the molecules is selected. Within the subset, all the molecules possess the at least one property. A plurality of marker molecules is selected from the subset.

A method of using such a model may comprise comparing the structural characteristics of a candidate molecule with an unknown property with the structural characteristics the marker molecules.

In another embodiment, there is a method of predicting whether or not a molecule is highly protein bound in serum. The structural similarity of the molecule to a plurality of marker molecules is numerically defined, wherein all the marker molecules are known to be highly protein bound in serum. The structure similarities are compared to a corresponding plurality of numerical thresholds associated with each of the plurality of marker molecules.

DETAILED DESCRIPTION OF THE PREFERRED EMBODIMENT

Figure 1:
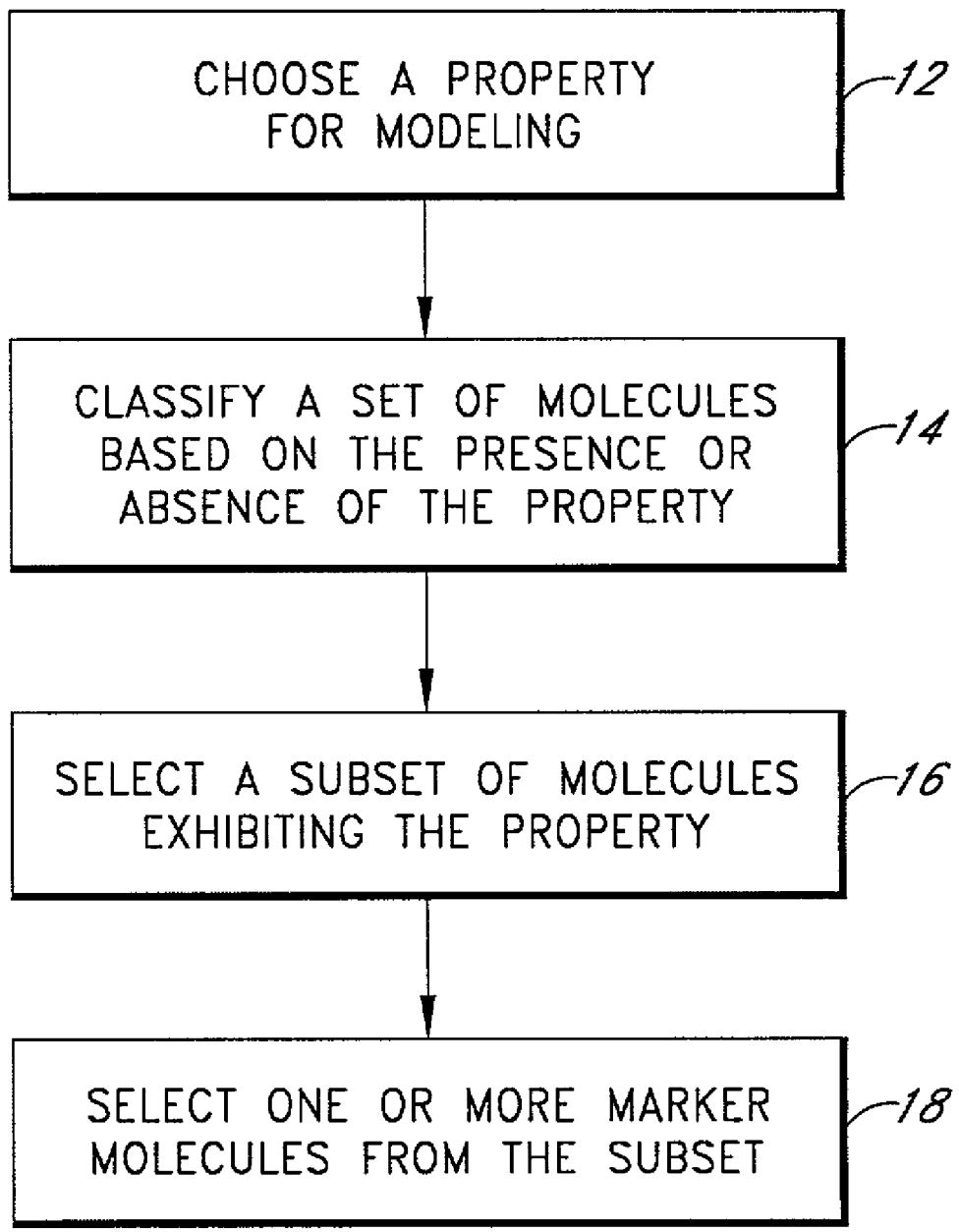
FIG. 1 is a flowchart of a method that selects marker molecules for a model predicting molecular activity.

Embodiments of the inventions will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

The inability of previously developed models to predict structurally related aspects of protein binding seems to be caused at least in part by the variety of possible specific interactions between a given molecule and the serum proteins. Human serum albumin (HSA), the main binding protein, has at least three binding sites with moderate, yet overlapping specificity for binding specific structural classes. These are known as site I—the warfarin site, site II—the benzodiaopenes/NSAIDS site, and site III—the digitoxin site. Allosteric interactions between compounds binding to different HSA binding sites further complicate matters. The binding specifications of the HSA sites are another important factor. Valproic acid and tolbutamide bind to both HSA Sites I and II. Suprofen binds to HSA site II, yet suprofen methyl ester binds to HSA site I. The HSA site I (the warfarin binding site) is large enough to be divided into three separate regions, based upon displacement studies of the molecules binding to those regions: warfarin, azapropazone, and n-butyl pABE. Medium chain fatty acids (C-6 to C-12), but no medium chain aliphatic amines, have been shown to displace fluorescent probes and marker molecules binding to HSA site II, indicating positive charge at physiological pH precludes HSA site II binding. The variety of other blood proteins adds further complexity.

In developing the systems and methods described herein, it was postulated that methods which attempt to describe the entirety of the chemical space of interest using only a few hundred molecules simply do not sample the smaller area of chemical space related to the particular property of interest well enough to be able to make good predictions. Methods such as the hashkey and nearest neighbor approaches exemplify such approaches. In developing a model for protein binding prediction which does not suffer from this drawback, a model development method having wide applicability to activity prediction has been created. Applying the method to the protein binding problem has further resulted in an improved protein binding prediction model.

In advantageous embodiments of the model development method, a set of marker molecules is selected, all of which possess the chemical/biological property of interest, thus providing high coverage of a small chemical space associated with the property. The model development method is most advantageously applied to the prediction of specific molecular interactions such as protein-ligand interactions. In many of these cases, there are a specific set of possible combinations of structural features and shapes that allow for a specific interaction, whereas there are an almost infinite number of reasons why a molecule will not interact with a protein. By selecting marker molecules associated with the property of interest, there is a better chance of predictive success, because the model will be predicting the presence of a few specific interactions, rather than predicting all possible interactions. In some embodiments, the method includes selecting a training set of molecules some of which possess the property of interest and some of which do not. A set of marker molecules used for prediction is selected only out of those molecules of the training set that possess the property. Advantageous methods of choosing these marker molecules are set forth below.

Using the principles of predictive model development described herein, a model for classifying compounds as highly protein bound (>90% bound) or not highly protein bound (<90% bound) was created. The model development methods are thus described below using a protein binding model as one example application. The model development methods of the invention may also be applied to the creation of other prediction models, such as models to predict CYP450 metabolism, inhibition, and activation, as well as p-Glycoprotein efflux.

Referring now to FIG. 1, a method for constructing a model for predicting molecular behavior using marker molecules begins at a process block 12. At the process block 12, the property of interest that is to be predicted for the molecules with unknown properties is determined. In one embodiment described in detail herein, the property of interest is high protein binding.

The method next advances to the process block 14 where a reference ("training") set of molecules is classified according to the property of interest. The larger the training set of molecules is (>50 preferably), the better the method should perform. Preferably each of the molecules in the training set has a known binary classification for the property of interest. A training set for molecules where the property of interest is protein binding, for example, can be classified into molecules that possess high protein binding and molecules that possess low protein binding. For illustration, an example training set of ten molecules for a protein binding prediction model may be as follows:

| Molecule | % Protein Bound | Classification |
|---|---|---|
| CLONIDINE | 30.0% | 0 |
| DIAZEPAM | 98.7% | 1 |
| FLURBIPROFEN | 99.5% | 1 |
| HYDROCHLOROTHIAZIDE | 58.0% | 0 |
| LISINOPRIL | 0.0% | 0 |
| MINOCYCLINE | 76.0% | 0 |
| NAPROXEN | 99.7% | 1 |
| PYRIMETHAMINE | 87.0% | 0 |
| RIMANTADINE | 40.0% | 0 |
| WARFARIN | 99.0% | 1 |

The method next advances to a process block 16, where a subset of the training set of molecules is chosen such that the subset includes the molecules in the training set that have the desired property of interest. In one embodiment, molecules in this subset are referred to as Desired Target Class ("DTC") molecules. In the protein binding example described herein, molecules with protein binding greater than or equal to 90% are considered highly protein bound and are thus classified as DTC molecules. Using the example training set above, it can be seen that four of the ten training set molecules are DTC molecules.

The method next advances to a process block 18 where a plurality of marker molecules from the subset is selected. By selecting marker molecules only from the smaller set of DTC molecules, rather than from the entire training set, the method uses information from a larger data set to identify a set of marker molecules which provide high coverage of a relatively small chemical space associated only with the property of interest. It has been found that this results in a more accurate model for predicting the presence of the property in other molecules with unknown behavior.

Figure 2:
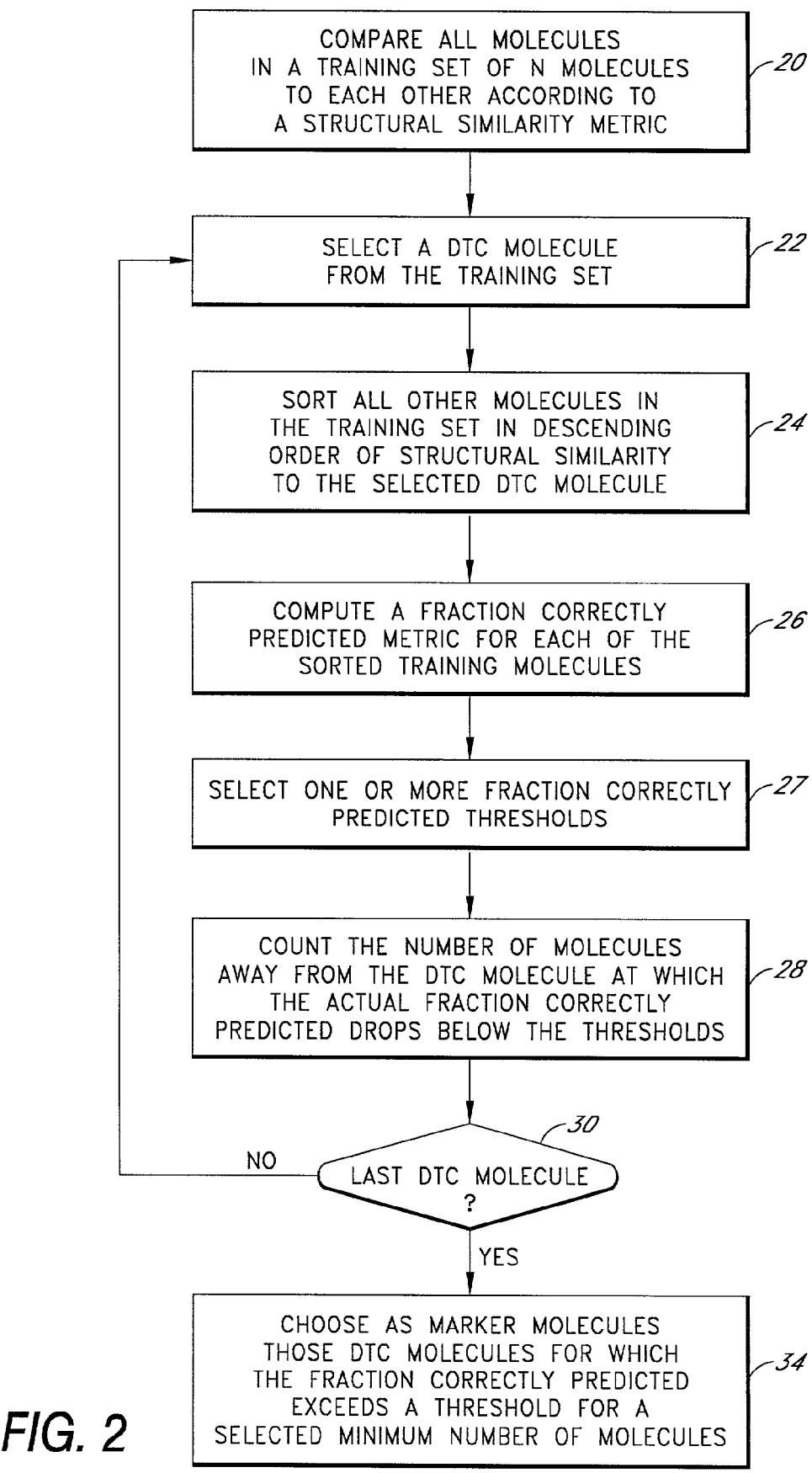
FIG. 2 is a flowchart of a method for selecting a set of marker molecules.

FIG. 2 illustrates one specific method for selecting a set of marker molecules from the DTC molecules in the process block 18 of FIG. 1. The method begins with the process block 20, where all the molecules in the training set are compared to each other using a structural similarity metric which produces a numerical measure of the similarity of a pair of molecules. This metric may be derived from any of a wide variety of structural similarity comparison methods, including comparisons of atomic spatial arrangements in three, two, or one dimensional representations of the molecules. Descriptor and/or molecular fragment based comparisons may also be used to numerically define structural similarity between molecule pairs. Which metric is best may depend on the property to be predicted, as well as other considerations such as desired computational speed of model execution once the model is created. In one embodiment, comparisons of atomic spatial arrangement using one dimensional molecular representations are utilized to derive a numerical measure of molecular similarity. Embodiments of this method are described in detail in U.S. application Ser.

Nos. 09/770,510 and 09/773,281 filed on Jan. 25, 2001 and Jan. 31, 2001 respectively, and entitled One-Dimensional Molecular Representations and Similarity Calculations." The disclosures of these applications are hereby incorporated by reference in their entireties.

The similarity measurements may be stored as a similarity matrix. The similarity matrix is an N×N matrix where N is the number of molecules in the training set. The following example is a similarity matrix where N=10, using the example training set described above wherein the molecules are Clonidine, Diazepam; Flurbiprofen; Hydrochlorothiazide, Lisinopril; Minocycline; Naproxen, Pyrimethamine, Rimantadine, and Warfarin, and the DTC molecules which are highlighted are Diazepam, Flurbiprofen, Naproxen, and Warfarin:

molecules are also DTC molecules. N is then iteratively selected to be 1, 2, 3, and so on, up through the total number of training set molecules.

In the sorted column of training set molecules for the DTC molecule Flurbiprofen illustrated above, for example, the FCP for the closest molecule (also Flurbiprofen) would be 1 because 100% of the molecules at least as close or closer to Flurbiprofen in structural similarity to Flurbiprofen are DTC molecules. For Naproxen, the FCP would also be 1, because 100% of the molecules as close or closer than Naproxen in structural similarity to Flurbiprofen are DTC molecules. For Diazepam, the FCP would again be 1 for the same reason. However, for Pyrimethamine, the FCP would be 0.75, because Pyrimethamine is not a DTC molecule and thus only 75% of the molecules as close or closer to Flurbiprofen

|  | Clonidine | Diazepam | Flur-Biprofen | Hydrochlorothiazide | Lisinopril | Minocycline | Naproxen | Pyrimeth-Amine | Rimantadine | Warfarin |
|---|---|---|---|---|---|---|---|---|---|---|
| Clonidine | 1 | 0.41758 | 0.37902 | 0.34227 | 0.24832 | 0.32348 | 0.35465 | 0.43861 | 0.19814 | 0.37184 |
| Diazepam | 0.41758 | 1 | 0.60247 | 0.40735 | 0.30301 | 0.35219 | 0.41351 | 0.47554 | 0.09522 | 0.53036 |
| Flurbiprofen | 0.37902 | 0.60247 | 1 | 0.31634 | 0.40497 | 0.30715 | 0.61548 | 0.52046 | 0.07745 | 0.45032 |
| Hydrochloro-thiazide | 0.34227 | 0.40735 | 0.31634 | 1 | 0.23676 | 0.24821 | 0.35748 | 0.25796 | 0.09916 | 0.28452 |
| Lisinopril | 0.24832 | 0.30301 | 0.40497 | 0.23676 | 1 | 0.16383 | 0.28765 | 0.2931 | 0.23981 | 0.2818 |
| Minocycline | 0.32348 | 0.35219 | 0.30715 | 0.24821 | 0.16383 | 1 | 0.2967 | 0.32192 | 0.20166 | 0.30291 |
| Naproxen | 0.35465 | 0.41351 | 0.61548 | 0.35748 | 0.28765 | 0.2967 | 1 | 0.41259 | 0.08076 | 0.45497 |
| Pyri-Methamine | 0.43861 | 0.47554 | 0.52046 | 0.25796 | 0.2931 | 0.32192 | 0.41259 | 1 | 0.04208 | 0.45099 |
| Rimantadine | 0.19814 | 0.09522 | 0.07745 | 0.09916 | 0.23981 | 0.20166 | 0.08076 | 0.04208 | 1 | 0.0365 |
| Warfarin | 0.37184 | 0.53036 | 0.45032 | 0.28452 | 0.2818 | 0.30291 | 0.45497 | 0.45099 | 0.0365 | 1 |

Next, at block 22, a DTC molecule is selected. The method next advances to a process block 24, where for the selected DTC molecule, all the other molecules in the training set are sorted according to descending structural similarity to each DTC molecule. For instance, the training set molecules are sorted in descending structural similarity to the DTC molecule Flurbiprofen, producing a sorted column appearing as follows:

|  | Flurbiprofen |
|---|---|
| Flurbiprofen | 1 |
| Naproxen | 0.61548 |
| Diazepam | 0.60247 |
| Pyrimethamine | 0.52046 |
| Warfarin | 0.45032 |
| Lisinopril | 0.40497 |
| Clonidine | 0.37902 |
| Hydrochlorothiazide | 0.31634 |
| Minocycline | 0.30715 |
| Rimantadine | 0.07745 |

The process then advances to a process block 26 where a fraction-correctly-predicted (FCP) metric is calculated for each of the training set molecules with respect to the selected DTC molecule. The FCP value for the training set molecule A with respect to DTC molecule B is defined as the number of DTC molecules that have a structural similarity at least as great with respect to DTC molecule B as does training set molecule A, divided by the total number of training set molecules that have a structural similarity at least as great with respect to DTC molecule B as does training set molecule A. The FCP thus characterizes, for the N closest molecules to DTC molecule B, what fraction of those N molecules are DTC molecules. For Warfarin, the FCP would be 0.8 because Warfarin is a DTC molecule, and thus 4 out of the closest 5 molecules in structural similarity to Flurbiprofen are DTC molecules. An exemplary FCP matrix for the DTC molecules Diazepam, Flurbiprofen, Naproxen, and Warfarin follows:

| Diazepam | Flurbiprofen | Naproxen | Warfarin |
|---|---|---|---|
| 1 | 1 | 1 | 1 |
| 1 | 1 | 1 | 1 |
| 1 | 1 | 1 | 1 |
| 0.75 | 0.75 | 1 | 0.75 |
| 0.6 | 0.8 | 0.8 | 0.8 |
| 0.666667 | 0.666667 | 0.666667 | 0.666667 |
| 0.571429 | 0.571429 | 0.571429 | 0.571429 |
| 0.5 | 0.5 | 0.5 | 0.5 |
| 0.444444 | 0.444444 | 0.444444 | 0.444444 |
| 0.4 | 0.4 | 0.4 | 0.4 |

Next, at block 27, one or more thresholds for the FCP value are selected. The method next advances to a process block 28 where values for a metric, referred to herein as MOLCNT, are determined. The series of MOLCNT values for a DTC molecule are the number of molecules away from a selected DTC molecule in the descending sorted order at which point the FCP drops below a selected FCP threshold. The value for MOLCNT for each DTC molecule will therefore increase as the selected threshold for FCP is decreased, and several different values for MOLCNT will be determined for each DTC molecule. In essence, the MOLCNT value answers the question: How many molecules away from DTC molecule A can one go before the predictive accuracy drops below threshold X? A series of different thresholds are advantageously selected, and thus a series of different MOLCNT values are computed for the selected DTC molecule.

In addition, a similarity cutoff value is also selected for each MOLCNT value. The similarity cutoff is the value of the similarity metric between the DTC molecule and the molecule which is the MOLCNT distance away from the DTC molecule.

At block 30, it is determined whether or not the above process has been performed for each DTC molecule. If not, the method loops back to block 22, where another DTC molecule is selected.

A matrix can be constructed that includes the MOLCNT value and CUTOFF values for each DTC molecule at different iterations of thresholds for the FCP. In the simplified example with ten training set molecules that follows, the threshold is decremented from 100% to 55% in increments of 5%. In another embodiment described in additional detail below, the threshold is decremented to 75% from 100% in 1% increments because accuracy tends to diminish too much at the expense of spatial coverage at thresholds below 75%. The following exemplary MOLCNT matrix displays the MOLCNT and CUTOFF for the DTC molecules Diazepam, Flurbiprofen, Naproxen, and Warfarin:

Flurbiprofen satisfy this criteria, thus becoming a second possible set of marker molecules. In this case, a test compound would be predicted as being highly protein bound if its structural similarity to Naproxen was at least 0.41259, its similarity to Flurbiprofen was at least 0.45032, or if its structural similarity to Warfarin was at least 0.45032.

It can thus be appreciated that depending on the selection of minimum FCP and MOLCNT, different sets of marker molecules will be chosen from the set of DTC molecules. It is thus advantageous in producing a predictive model to select the best possible set of marker molecules from all of the possible sets. For the two examples given above, it may be noted that the model including only Naproxen as a marker molecule is 100% accurate in making predictions about all the training set molecules. In other words, every training set molecule having a similarity to Naproxen of at least 0.41351 is highly protein bound. Every training set molecule having a similarity to Naproxen of less than 0.41351 is not highly protein bound.

On the other hand, the model including Naproxen, Warfarin, and Flurbiprofen is not 100% accurate. Although all of the highly protein bound training molecules are correctly classified, the training set molecule Pyrimethamine is incorrectly classified as highly protein bound when in fact it is not

| FCP Threshold | MOLCNT and CUTOFF for Flurbiprofen | MOLCNT and CUTOFF for Naproxen | MOLCNT and CUTOFF for Warfarin | MOLCNT and CUTOFF for Diazepam |
|---|---|---|---|---|
| 1 | 3, 0.60247 | 4, 0.41351 | 3, 0.45497 | 3, 0.53036 |
| .95 | 3, 0.60247 | 4, 0.41351 | 3, 0.45497 | 3, 0.53036 |
| .90 | 3, 0.60247 | 4, 0.41351 | 3, 0.45497 | 3, 0.53036 |
| .85 | 3, 0.60247 | 4, 0.41351 | 3, 0.45497 | 3, 0.53036 |
| .80 | 3, 0.60247 | 4, 0.41351 | 3, 0.45497 | 3, 0.53036 |
| .75 | 3, 0.60247 | 5, 0.41259 | 3, 0.45497 | 3, 0.53036 |
| .70 | 5, 0.45032 | 5, 0.41259 | 5, 0.45032 | 4, 0.47554 |
| .65 | 6, 0.40497 | 6, 0.35748 | 6, 0.37184 | 4, 0.47554 |
| .60 | 6, 0.40497 | 6, 0.35748 | 6, 0.37184 | 6, 0.41351 |
| .55 | 7, 0.37902 | 7, 0.35465 | 7, 0.30291 | 7, 0.40735 |

After these values are computed, the marker molecules can be selected at block 34 of FIG. 2. In this embodiment, a set of marker molecules is defined as every DTC molecule having a MOLCNT of equal to or greater than a selected value while maintaining a selected minimum FCP threshold. Once this set of marker molecules is selected, predictions are made by comparing the structural similarity of a compound with unknown behavior to each of the marker molecules. If the similarity between the test molecule and any of the marker molecules exceeds the CUTOFF value associated with any of the marker molecules at the minimum FCP and MOLCNT, then the test molecule is predicted to have the property.

For example, the marker molecules could be chosen to be all DTC molecules having an FCP of at least 0.75 for a MOLCNT distance of at least four molecules. From the above table, it can be seen that only Naproxen satisfies this criteria, so only Naproxen would be selected as a marker molecule under those conditions. The CUTOFF value associated with this FCP for Naproxen is 0.41351. Thus, any unknown compound with a structural similarity metric of 0.41351 when compared to Naproxen would be classified as highly protein bound.

Another possibility would be to select as marker molecules all DTC molecules having an FCP of at least 0.70 for a MOLCNT distance of at least five molecules. From the table above, it can be seen that Naproxen, Warfarin, and (although it is close, at 87%). Thus, the marker molecule set containing only Naproxen may be considered the better of the two proposed sets of marker molecules, as it is the most accurate in classifying training set molecules. A general process of selecting the "best" set of marker molecules from the different possible selected sets is described below with reference to FIG. 4.

It can be appreciated from the above discussion that the MOLCNT value is used advantageously to ensure that the predictions the model makes are not only accurate, but also representative of substantial spatial coverage. For example, molecule A, which is 99% protein bound, may be 80% correct in predicting molecules which are greater or equal to 90% bound within similarity CUTOFF B. However, out of a large data set, this 80% accuracy extends for four molecules out from molecule A making molecule A not very useful. On the other hand, molecule C is also 80% correct in predicting molecules which are greater or equal to 90% protein bound within similarity CUTOFF D, but out of a large data set this accuracy extends out 36 molecules. Therefore, MOLCNT is useful in distinguishing a molecule C from a molecule A in order to provide a much better spatial coverage. When a large data set is used, estimation of coverage over a large space becomes even more important in order to better predict molecular properties. The MOLCNT will increase as the threshold for the FCP decreases.

Figure 3:
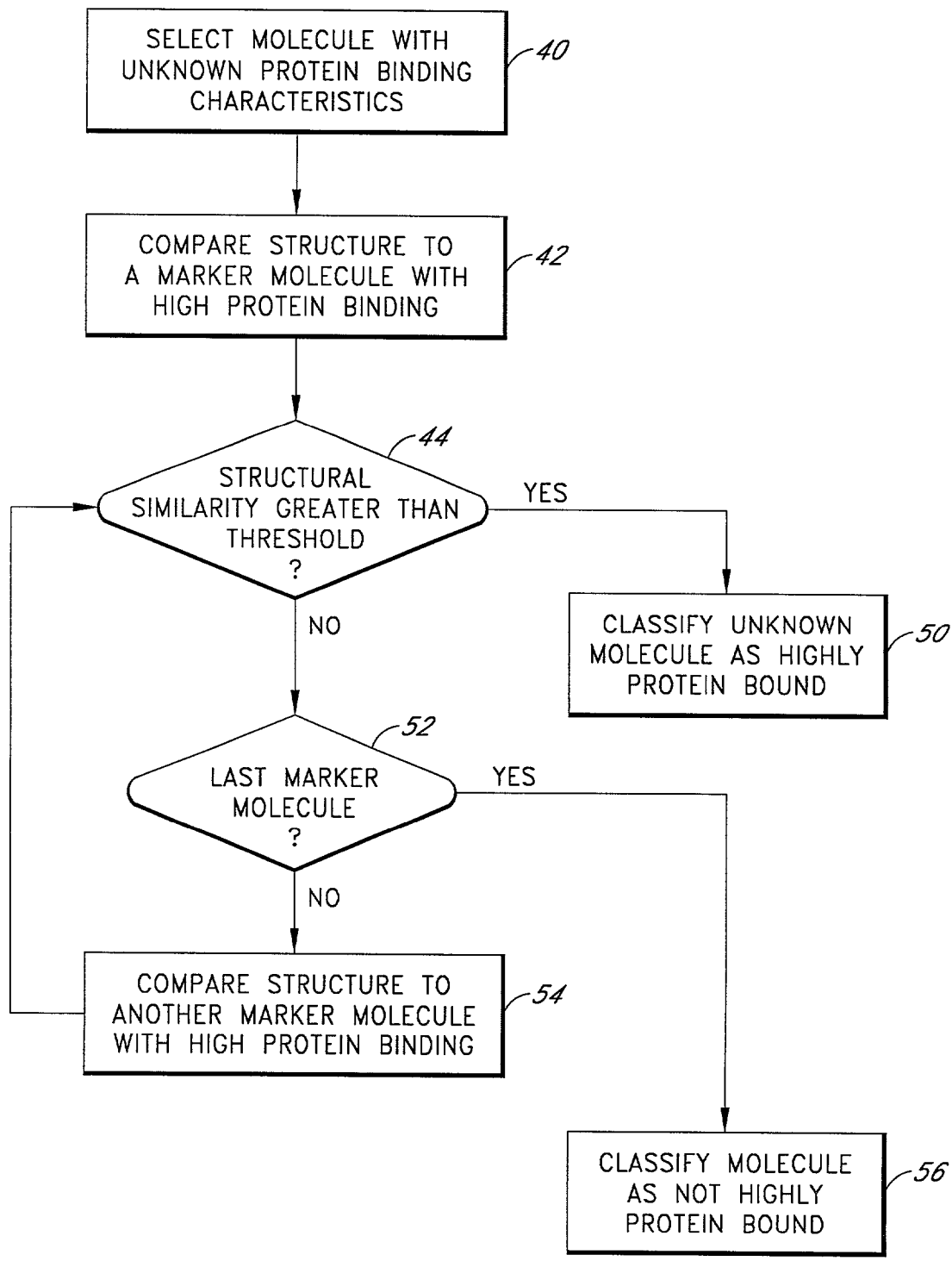
FIG. 3 illustrates a method for classifying a molecule as being highly protein bound or not highly protein bound.

Referring now to FIG. 3, a method is shown for using a protein binding model created in accordance with the above described principles. The method begins at a process block 40 where a candidate molecule is selected with unknown protein binding characteristics. The method next advances to a process block 42 where the structure of the candidate molecule is compared to a first one of the selected marker molecules. A variety of comparison methods can be used to compare structure. In one embodiment, the one dimensional comparison method is used as discussed above. The method next advances to a decision block 44 where the method determines if the structural similarity between the candidate molecule and the marker molecule is greater than a preselected threshold, which may advantageously be the CUTOFF value described above. If the structural similarity is greater than the threshold, the method advances to a process block 50 where the candidate molecule is classified as highly protein bound. If the structural similarity is not greater than the threshold, the method advances to a decision block 52 where the method determines if the last marker molecule has been analyzed. If the last marker molecule has been analyzed, then there were no marker molecules having a structural similarity to the candidate molecule greater than their respective thresholds. Therefore, the method advances to a process block 56 where the candidate molecule is classified as not highly protein bound because there is no marker molecule having structural similarity to the candidate molecule greater than the threshold. However, if the last marker molecule has not been compared to the candidate molecule at the decision block 52, then the method advances to a process block 54 where the structure of a next marker molecule is compared to the candidate molecule. The method than advances back to the decision block 44 to determine if the structural similarity is greater than the threshold. This process is repeated, if desired, for all of the marker molecules. If the structural similarity between the candidate molecule and any of the marker molecules exceeds the corresponding threshold (e.g. the corresponding CUTOFF value), the candidate molecule will be classified as highly protein bound.

It will be understood that in most applications, a general purpose computer is used to implement the methods described herein. The general purpose computer will include and/or have access to one or more memories which store molecular structural information which is stored in a data storage device such as a CD-ROM, magnetic disk, semiconductor integrated circuit memory, or the like. The computer will also include a processor configured for accessing the data base, performing structural similarity calculations, performing comparisons between calculated similarities and similarity threshold values, etc. Also included will be input and output devices for user interface such as keyboards, graphic display, printer, etc. The commands which configure such a general purpose computer to implement the methods of the invention are stored on a computer readable medium such as a CD-ROM for access by the general purpose computer.

Figure 4:
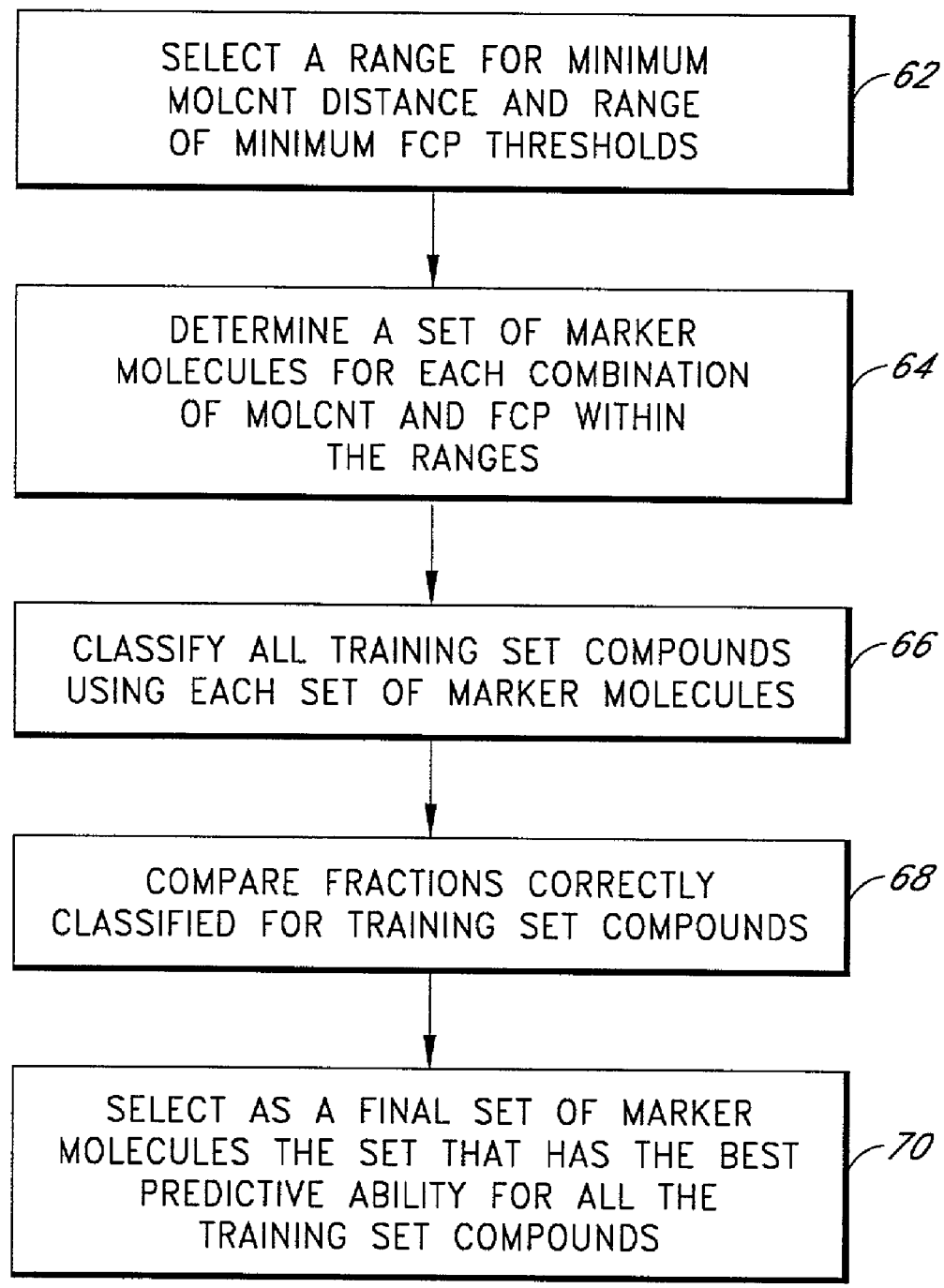
FIG. 4 is a flowchart of a method for determining the best predictive set of marker molecules amongst a plurality of sets of marker molecules.

FIG. 4 illustrates a process for selecting a highly predictive set of marker molecules from different sets of marker molecules. In one embodiment, the method starts at block 62 by selecting a range of minimum MOLCNT distances and a range of minimum FCP thresholds. In one advantageous embodiment, the range of MOLCNT is 5 to 15, and the range of FCP thresholds is 100% to 75%. At block 64, a set of marker molecules is selected in accordance with the method described above with reference to FIG. 2 for different combination of MOLCNT and FCP within the ranges. For example, a first set of marker molecules may be selected that have an FCP of 100% for at least five molecules out in structural similarity. A second set of marker molecules is then selected that have an FCP of at least 99% for at least five molecules out in structural similarity. This process may be repeated for all combinations of MOLCNT and FCP, such as FCP of at least 80% for at least ten molecules out, and FCP of 85% for seven molecules out, etc. For a range of 5–15 for MOLCNT and 100% to 75% for FCP, this will produce 286 sets of marker molecules (with some sets possibly being identical, of course). At this point, the distinct marker molecule sets are selected. Some sets may contain redundant pairs of molecules that are highly structurally similar, where the presence of both is unnecessary. One of these will advantageously be removed.

Next, at block 66, each set of marker molecules is used to classify all of the molecules in the training set, and at block 68, the predictive results are compared. Because the training set may contain different numbers of DTC and non-DTC molecules, the predictive accuracy is advantageously evaluated separately for DTC training molecules and non-DTC training molecules. At block 70, the final "best" set of marker molecules is selected that has the best overall predictive ability for both non-DTC training molecules and DTC training molecules.

The model creation principles described above were used to create a robust and surprisingly accurate protein binding prediction model. The above simplified example includes 10 training dataset molecules. However, to create a better model, the training dataset was composed of most of the 260 compounds listed in *Goodman & Gilman's The Pharmacological Basis of Therapeutics,* $9^{th}$ ed.[31] having percent protein bound (% PB) data. The following compounds were excluded because they lacked % PB values or belonged to an unusual structural class: atracurium, auranofin, azathioprine, bleomycin, bretylium, busulfan, capreomycin, carboplatin, carmustine, cisplatin, clemastine, dobutamine, enoxacin, ethanol, foscarnet, gold sodium thiomalate, isosorbide-5-mononitrate, isosorbide dinitrate, levodopa, levonorgestrel, methohexital, methylprednisolone, nalbuphine, naloxone, neostigmine, nitroglycerin, pancuronium, pipecuronium, prednisolone, prednisone, pyridostigmine, scopolamine, tubocurarine, vecuronium.

A similarity matrix was prepared using one-dimensional representations as described above. The one-hundred six DTC molecules from this dataset that had high protein binding characteristics were separated, and the sorting, FCP, MOLCNT, and CUTOFF calculations as set forth above were performed. Sets of marker molecules were selected by taking all possible combinations of MOLCNT greater than or equal to 5 through 15 and an FCP of 100% to 75% in 1% increments, thus creating 286 possible sets of marker molecules. Non-redundant sets were tested for predictive accuracy over all of the training molecules. The set with the best predictive accuracy, which was the set having MOLCNT at least 6 while maintaining an FCP of at least 82%, is set forth below:

| Marker Molecules | % PB | Similarity Cutoff |
|---|---|---|
| AMLODIPINE | 93 | 0.4255 |
| BENAZEPRIL | 97 | 0.4583 |
| BUMETANIDE | 99 | 0.5450 |
| CHLORDIAZEPOXIDE | 96.5 | 0.6301 |

-continued

| Marker Molecules | % PB | Similarity Cutoff |
|---|---|---|
| CLOFIBRATE | 96.5 | 0.5177 |
| CLORAZEPATE | 96.9 | 0.5483 |
| DIAZEPAM | 98.7 | 0.6794 |
| DIFLUNISAL | 99.9 | 0.4766 |
| ETODOLAC | 99.1 | 0.4545 |
| FELODIPINE | 99.6 | 0.4348 |
| FLURAZEPAM | 96.6 | 0.5359 |
| FLURBIPROFEN | 99.5 | 0.5293 |
| FUROSEMIDE | 98.8 | 0.4692 |
| GLIPIZIDE | 98.4 | 0.4387 |
| GLYBURIDE | 99.8 | 0.4394 |
| HALOPERIDOL | 92 | 0.4829 |
| IMIPRAMINE | 90.1 | 0.8003 |
| ISRADIPINE | 97 | 0.4350 |
| ITRACONAZOLE | 99.8 | 0.3963 |
| KETOCONAZOLE | 99 | 0.4170 |
| KETOROLAC | 99.2 | 0.5705 |
| LORAZEPAM | 91 | 0.5701 |
| NABUMETONE | 99 | 0.5482 |
| NAPROXEN | 99.7 | 0.5378 |
| NICARDIPINE | 99 | 0.3727 |
| NIMODIPINE | 98 | 0.3649 |
| NITRENDIPINE | 98 | 0.5051 |
| NORDAZEPAM | 97.5 | 0.6898 |
| OXAZEPAM | 98.8 | 0.6399 |
| PAROXETINE | 95 | 0.4051 |
| PIMOZIDE | 99 | 0.5277 |
| PIROXICAM | 98.5 | 0.4484 |
| PRAZEPAM | 95.5 | 0.5440 |
| PROTRIPTYLINE | 92 | 0.7421 |
| SULINDAC | 94 | 0.5589 |
| TEMAZEPAM | 97.6 | 0.6675 |
| TOLMETIN | 99.6 | 0.5222 |
| TRAZODONE | 93 | 0.4748 |
| WARFARIN | 99 | 0.5083 |
| ZOLPIDEM | 92 | 0.5110 |

Within the training set of molecules, this predictive model was able to correctly classify 80.2% of the highly protein bound molecules, 68.2% of low protein bound molecules, and was 73.1% correct overall.

As noted previously, lipophilicity has been shown to be a significant component of protein binding. A refinement of the above model was thus made which takes lipophilicity directly into account as well. In the training set, 106 compounds have % PB≧90%. For compounds with AlogP98≧4.0, (wherein AlogP98 is a well known fragment based computational method of estimating logP for a compound) a large majority have % PB≧90%. For the training set, of 43 compounds with AlogP98≧4.0, 37 have % PB≧90% and six have % PB<90%. Once compounds surpass AlogP98 of 5.0, their % PB is almost always ≧95%. As a result of this analysis, a cutoff of AlogP98 of 4.0 was established; and in addition to the structural comparison procedures outlined above, compounds with AlogP98≧4.0 are predicted by the refined model to have % PB≧90%.

When AlogP98 was added, model prediction quality improved, and the combined similarity and AlogP98 model was able to correctly classify 80.2% of HPB molecules and 80.5% of LPB molecules, with overall correct accuracy of 80.4%. To summarize, this model will predict a molecule to be highly protein bound (≧90%) if that molecule has an AlogP98≧4.0 or the structural similarity in a one-dimensional representation to any of the 40 marker molecules set forth above exceeds that molecule's listed similarity cutoff. Molecules with AlogP98≧5.0 would be predicted to be >95% protein bound.

A test dataset was also assembled to verify model performance. The test molecules consisted of 121 orally available compounds in the Physician's Desk Reference (PDR) which were not in the training set and had % PB data. A final validation set was composed of 31 compounds which had experimental % PB data, but which were not part of either the training or test data sets.

Model performance on the test set of 121 orally available drugs listed in the Physician's Desk Reference (PDR) for which % PB data was available and which were not in the training set was very good. In the test set, 62 compounds have % PB≧90%. The model correctly predicted 82.8% of the highly protein bound, 80.7% of the low protein bound, and 81.8% of the PDR drugs overall.

For the validation dataset, the model was able to correctly predict 30 of 31 (96.8%) additional compounds, all of which had experimentally measured % PB≧90%, with 21 of the compounds having % PB≧98%.

Figure 5:
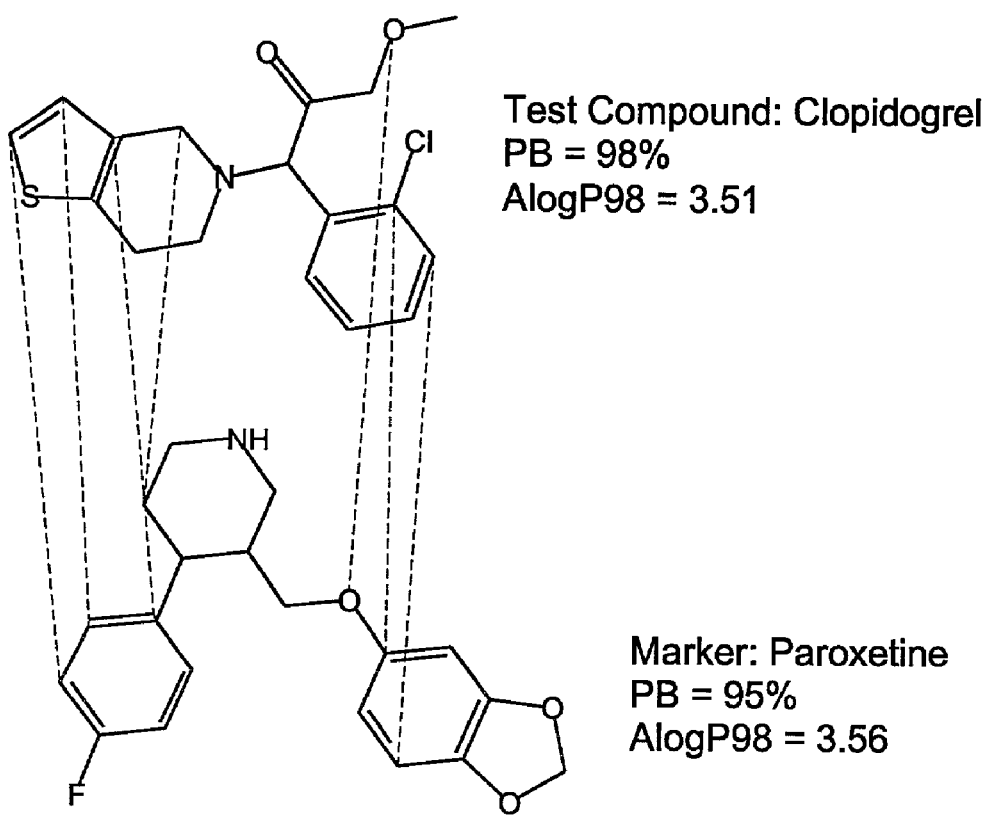
FIG. 5 illustrates a comparison between a candidate molecule and a marker molecule resulting in a prediction of high protein binding for the candidate molecule.

FIG. 5 shows a comparison between the marker molecule paroxetine, which is 95% protein bound, and the PDR test molecule clopidogrel, which is 98% protein bound. The structural similarity as calculated by the one-dimensional representation and comparison method described above is 0.439, which exceeds the similarity threshold of 0.4051 for paroxetine. In FIG. 5, the two molecules are shown aligned, with similar atoms in similar one-dimensional positions indicate by dashed lines.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computer-implemented method of selecting marker molecules that are for constructing a model for predicting whether a test molecule has a chemical or biological property of interest using said marker molecules that are known to possess said chemical or biological property of interest, said method comprising:
   classifying respective molecules in a training set of reference molecules as either possessing or not possessing said chemical or biological property of interest, wherein said classifying is based on experimental data;
   selecting, from said training set, a plurality of molecules that possess the chemical or biological property of interest as target molecules for potential selection as marker molecules for said model;
   selecting some of said target molecules as marker molecules for said model by evaluating the predictive accuracy of said potential marker molecules, wherein said evaluating comprises:
   computing a numerical value defining a measure of molecular structural similarity for each pair of molecules in said training set using a pre-defined structural similarity metric;
      selecting one of said target molecules (T);
      sorting all training set molecules in descending order of structural similarity to molecule T as defined by the computed numerical values;

defining, for a first one of said sorted training set molecules (M) a fractions-correctly-predicted metric as a ratio of A/B, wherein B is defined as the total number of training set molecules that have a computed numerical structural similarity to molecule T that is as large or larger than the computed numerical structural similarity between molecules T and M, and wherein A is defined as the number of training set molecules that both (1) have a computed numerical structural similarity with molecule T that is as large or larger than the computed numerical structural similarity between molecules T and M, and (2) possess the chemical or biological property of interest;

repeating the defining step for other sorted training set molecules;

choosing molecule T as a marker molecule if said number B and said ratio A/B are both above respective threshold values when computed during at least one of said defining steps; and outputting data indicating that molecule T has been chosen as a marker molecule.

2. The method of claim 1, additionally comprising repeating said choosing for a plurality of different threshold values.

3. The method of claim 1, comprising repeating said selecting a target molecule, sorting, defining and choosing steps for other molecules that possess the at least one chemical or biological property at a plurality of different threshold values so as to select a plurality of preliminary sets of marker molecules.

4. The method of claim 3, comprising choosing a final set of marker molecules by making molecular behavior predictions for all molecules in said training set using each one of said preliminary sets of marker molecules, and choosing as said final set of marker molecules the preliminary set that most accurately predicts molecular behavior of molecules of said training set.

5. The method of claim 1, wherein said threshold for B is 5, and said threshold for A/B is 1.

* * * * *